United States Patent [19]
Goodby et al.

[11] Patent Number: 5,578,242
[45] Date of Patent: Nov. 26, 1996

[54] THIO-ESTER COMPOUNDS AND MIXTURES AND DEVICES CONTAINING SUCH COMPOUNDS

[75] Inventors: John W. Goodby; Michael Hird; Kenneth J. Toyne; Alexander J. Seed; Damien G. McDonnell; Amarjit K. Samra, all of Hull, United Kingdom

[73] Assignee: The Secretary of State for Defence in Her Britannic Majesty's Government of the United Kingdom of Great Britain and Northern Ireland of Defence Research Agency, England

[21] Appl. No.: 416,737
[22] PCT Filed: Oct. 8, 1993
[86] PCT No.: PCT/GB93/02084
    § 371 Date: Apr. 12, 1995
    § 102(e) Date: Apr. 12, 1995
[87] PCT Pub. No.: WO94/09085
    PCT Pub. Date: Apr. 28, 1994

[30] Foreign Application Priority Data
Oct. 16, 1992 [GB] United Kingdom .................. 9221820

[51] Int. Cl.$^6$ .......................... C09K 19/52; C09K 19/34; C09K 19/32; G02F 1/13
[52] U.S. Cl. ................. 252/299.01; 252/299.61; 252/299.62; 252/299.64; 252/299.65; 252/299.66; 359/103
[58] Field of Search .................... 252/299.01, 299.61, 252/299.62, 299.64, 299.65, 299.66, 299.67; 359/103

[56] References Cited

U.S. PATENT DOCUMENTS 4,137,250  1/1979  Reynolds .......................... 352/299.01
4,372,871  2/1983  Toriyama et al. ................ 252/299.61
5,099,344  3/1992  Tsuboyama et al. ................ 359/100

FOREIGN PATENT DOCUMENTS 0184012  6/1986  European Pat. Off. .
2603293  8/1977  Germany .

OTHER PUBLICATIONS

CA 93:46138. 1980.

Primary Examiner—Shean C. Wu
Attorney, Agent, or Firm—Nixon & Vanderhye

[57] ABSTRACT

Liquid crystal compounds of the formula:

$$R^1-Z^1)_m-(Z^2)-X-(Z^3)-(Z^4)_n-R^2$$

These compounds may be mixed with other liquid crystal compounds to give liquid crystal mixtures which may then be used in liquid crystal devices. In the formula X is COS, CSS and CSO; each of $Z^1$, $Z^2$, $Z^3$, and $Z^4$ are independently phenyl, substituted phenyl, where substitution is lateral substitution selected from F, Cl, Br, $NO_2$, CN, NCS; naphthalene, substituted naphthalene, where substitution is lateral substitution selected from F, Cl, Br, $NO_2$, CN, NCS, $CH_3$; thiophene, pyridine and pyrimidine; each of $A^1$ and $A^2$ is independently selected from single bond, C≡C, CH=CH; $A^3$ is selected from C≡C and single bond; each of $R^1$ and $R^2$ are independently selected from CN, NCS, CH=C(CN)$_2$, C≡C—CN, C≡C—CF$_3$, alkyl, alkoxy, thioalkyl, alkenyl, and alkynyl; m and n are independently selected from 1 and 0, except where m and n are 0, X is COS and each of $R^1$ and $R^2$ are selected from alkyl and alkoxy, $A^3$ is a single bond and each of $Z^2$ and $Z^3$ is phenyl.

9 Claims, 7 Drawing Sheets

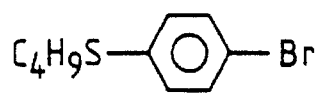 1
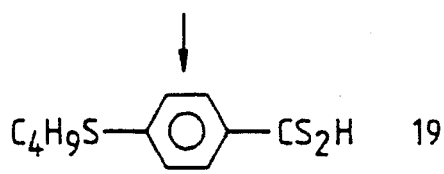 19   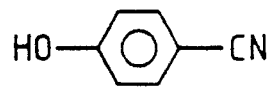
Fig.6.
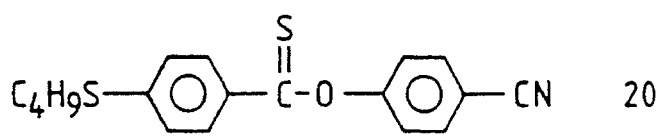 20
Fig.7.
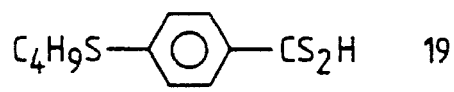 19   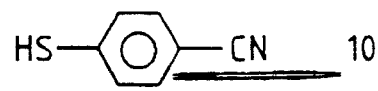 10
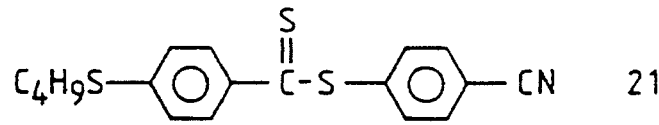 21
Fig.8.
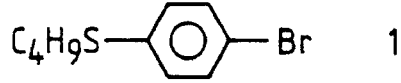 1   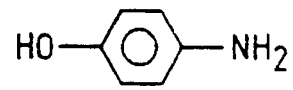
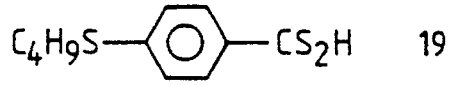 19   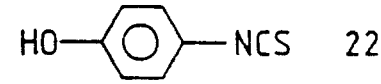 22
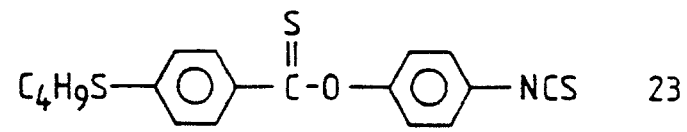 23

THIO-ESTER COMPOUNDS AND MIXTURES AND DEVICES CONTAINING SUCH COMPOUNDS

This application is a 371 3 PCT/GB93/02084, filed Oct. 8, 1993.

BACKGROUND OF THE INVENTION

This invention relates to compounds containing a thio-ester group, and in particular to thio-ester compounds having liquid crystalline properties. The invention also relates to use of thio-ester compounds in liquid crystalline materials, and to use of thio-ester compounds, and materials containing thio-ester compounds, in devices.

Liquid crystal materials and their uses in electro-optical display devices are well known. The most commonly used types of liquid crystal materials are those which can utilise their nematic properties within such devices as the Twisted Nematic (TN) device, Supertwist Nematic (STN) device and Electrically Controlled Birefringence (ECB) device.

Thio-ester compounds are known, and are described in for example S. R. Pandas et al, Synthesis, (1983), pp 605-621: Z-C Chen et al, Synthesis, (1988), pp 723-724; and B. S. Pedersen et al, Bull Soc. Chim. Belg., (1978) Vol 87 pp 293-297. Liquid crystalline thio-ester compounds are described in M. E. Neubert et al Mol. Cryst. Liq. Cryst. (1981) Vol 76, pp 43-77. Thio-ester compounds are also described in German patents DE 2603293, DD 0145914, Japanese patents JP 550023129, JP 560108761, JP 600163858, Isr. J. Chem., 1980, volume data 1979, volume 18 (3-4), pages 197-198; J. Prakt. Chem., 1979, volume 321 (4), pages 619-628.

Liquid crystal materials are generally mixtures of compounds which individually or together show a liquid crystal phase. A number of desirable characteristics are sought in such compounds and materials. Among these are chemical stability, persistence of appropriate liquid crystal phases over a wide temperature range preferably including room temperature, and for some devices a high birefringence ($\Delta n$) is sought.

BRIEF DESCRIPTION OF THE DRAWINGS

FIGS. 1-14 are flow diagrams giving typical synthesis routes to prepare the compounds of Formula I;

DESCRIPTION OF THE INVENTION

Figure 1:
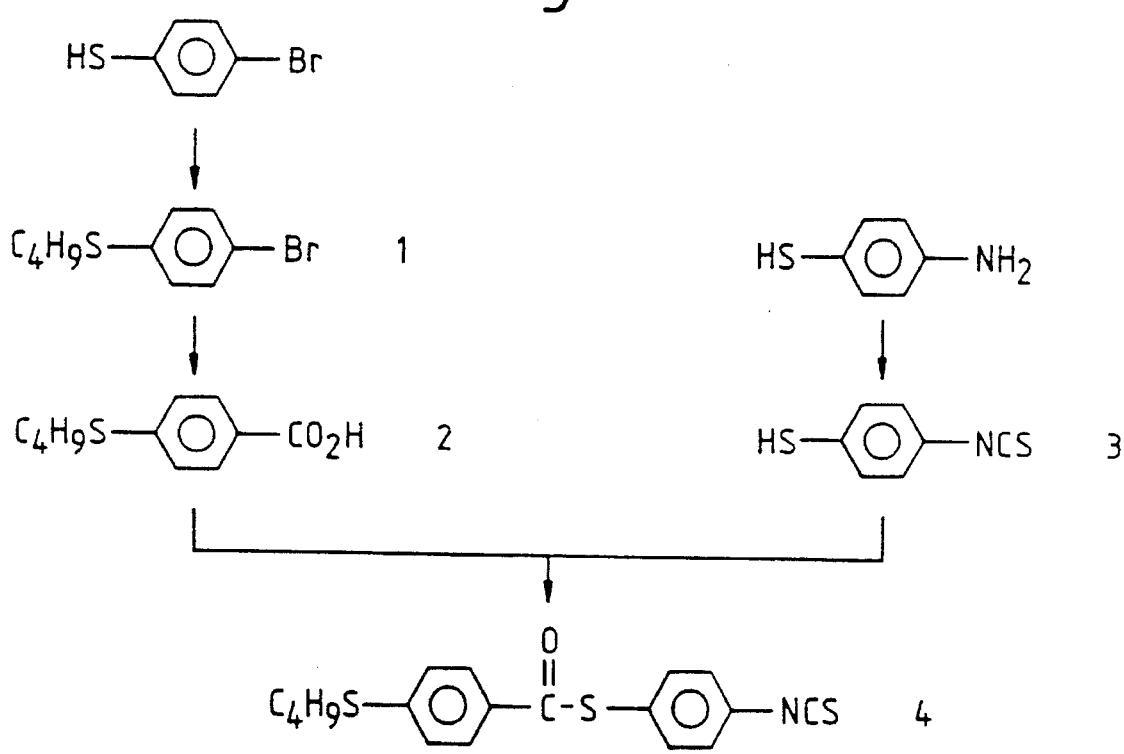
Figure 2:
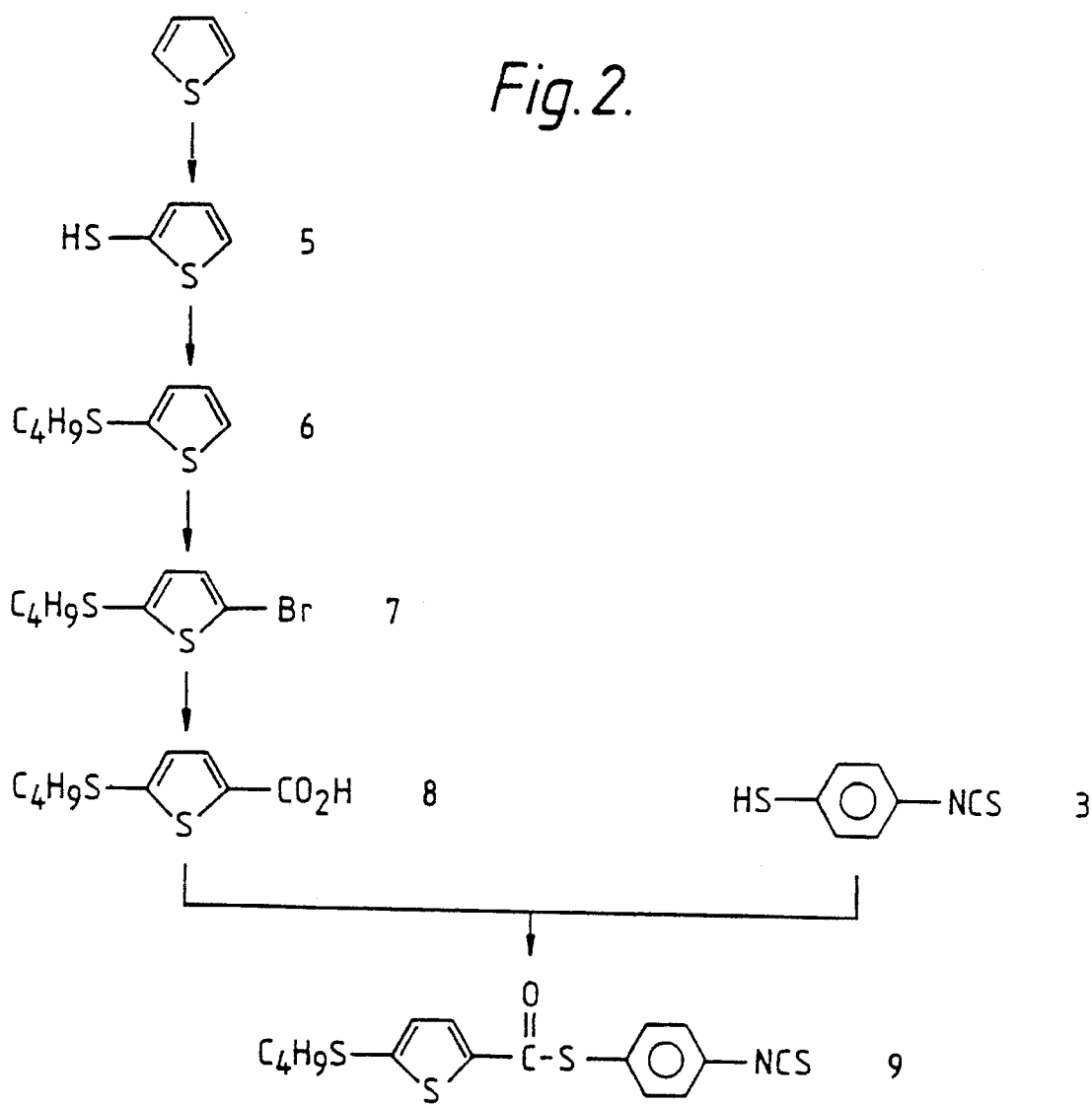
Figure 3:
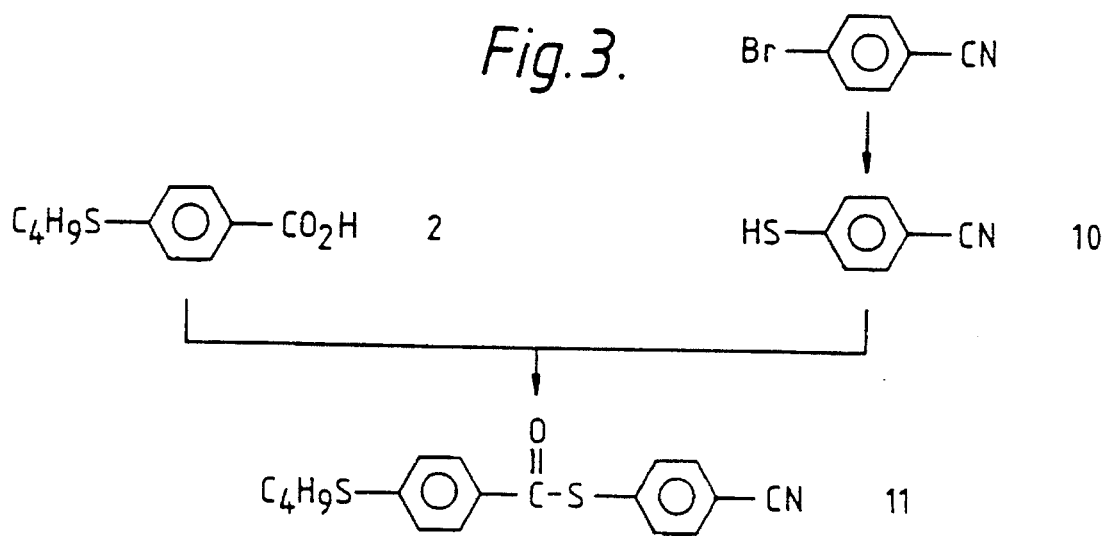
Figure 4:
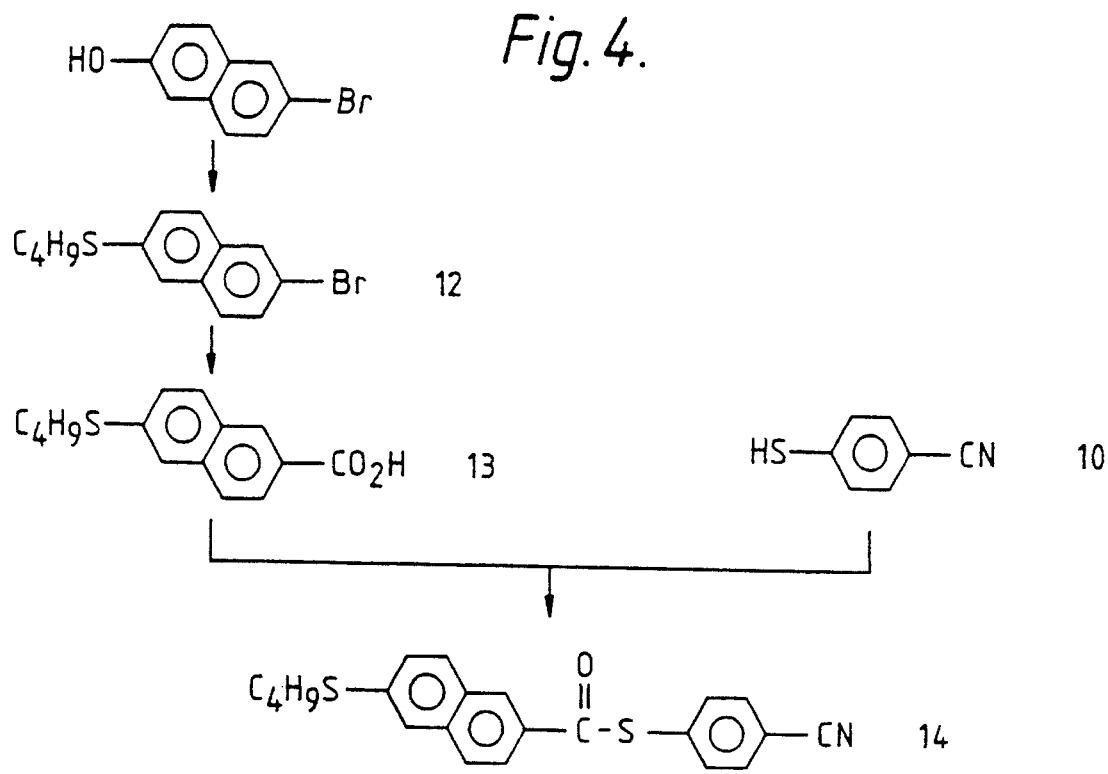
Figure 5:
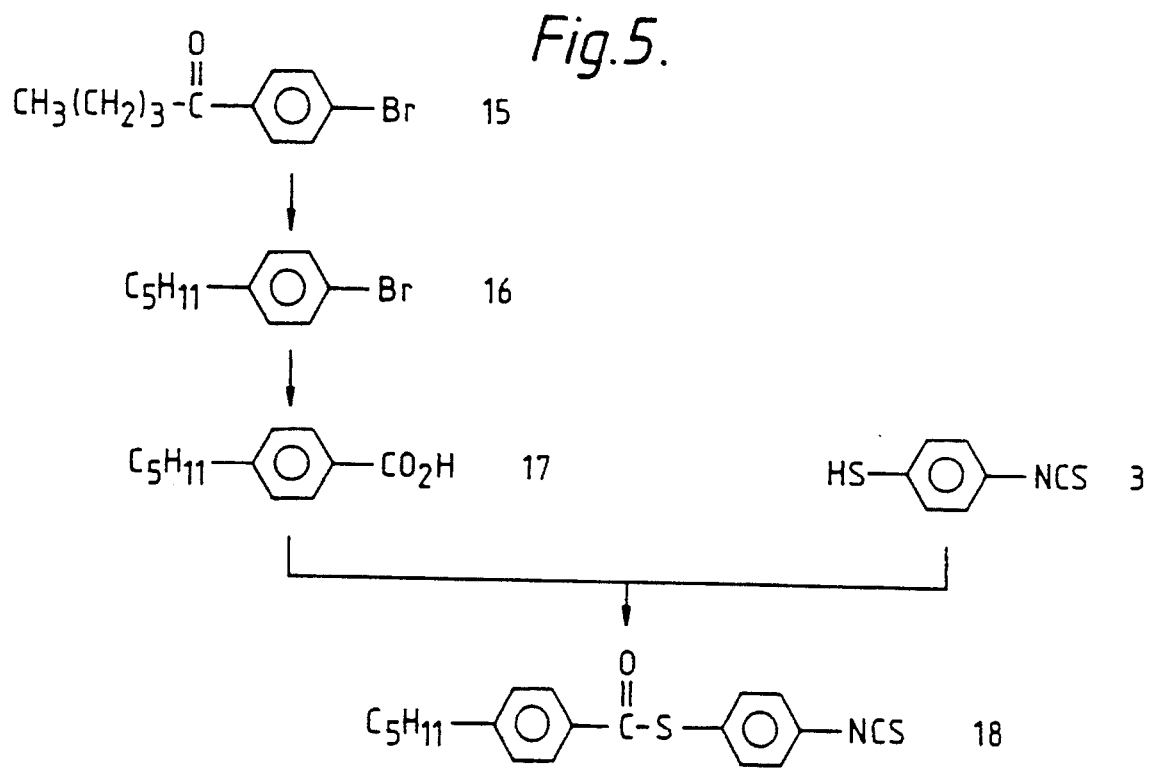
Figure 9:
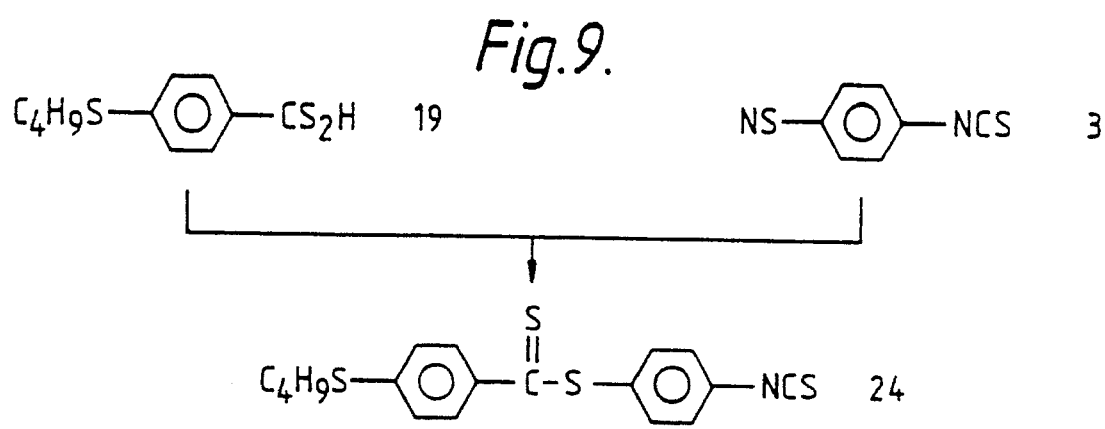
Figure 10:
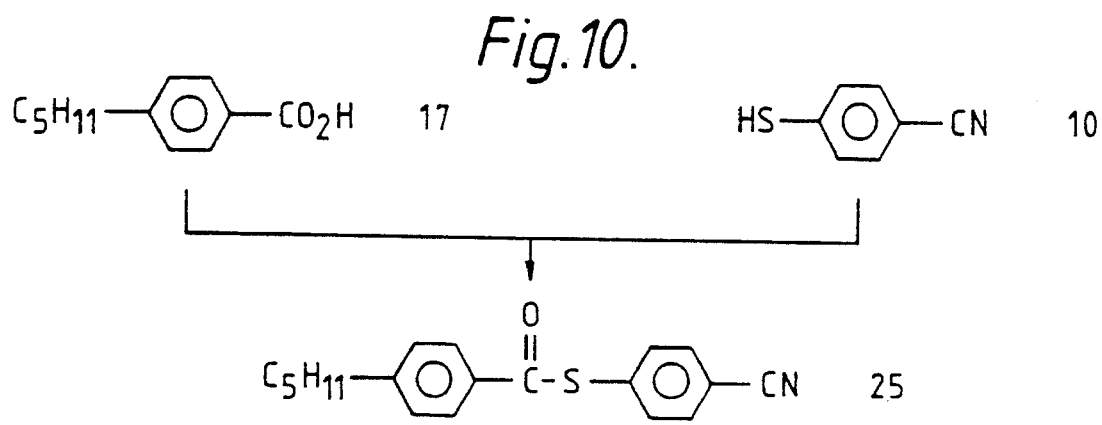
Figure 11:
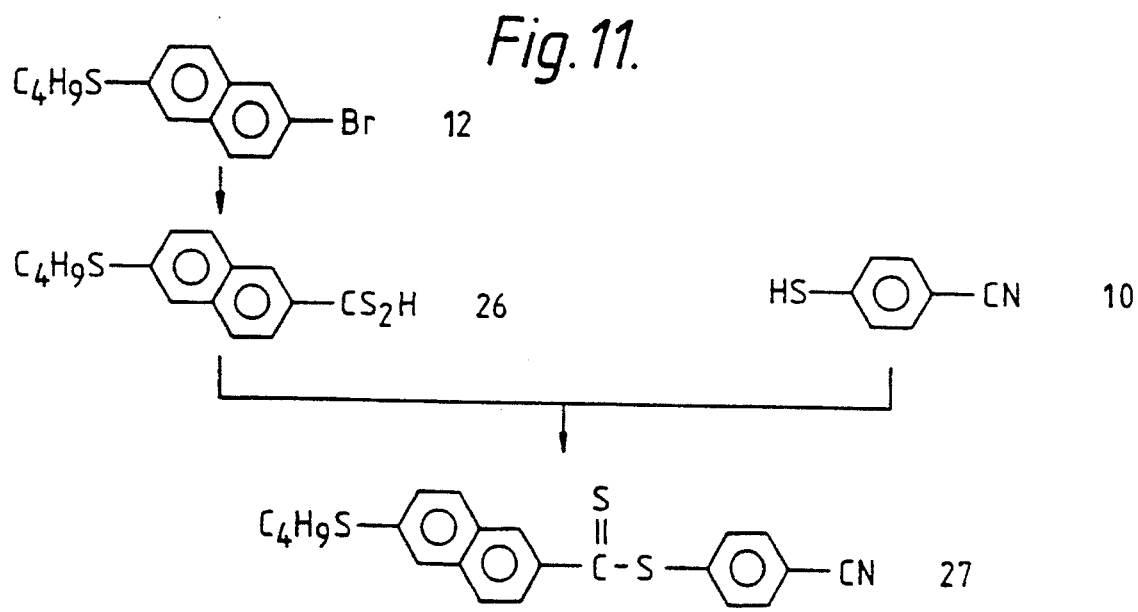
Figure 12:
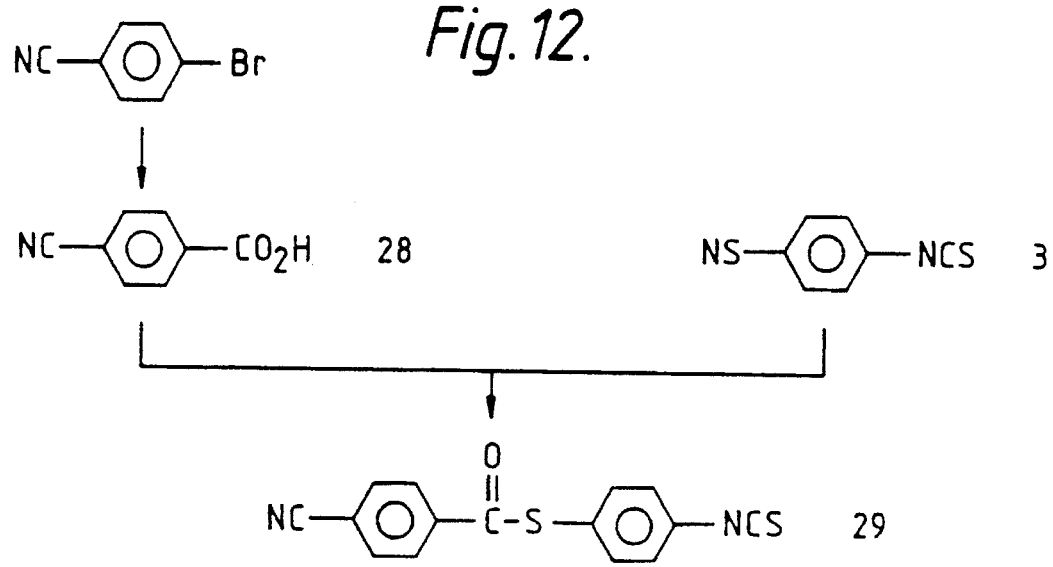
Figure 13:
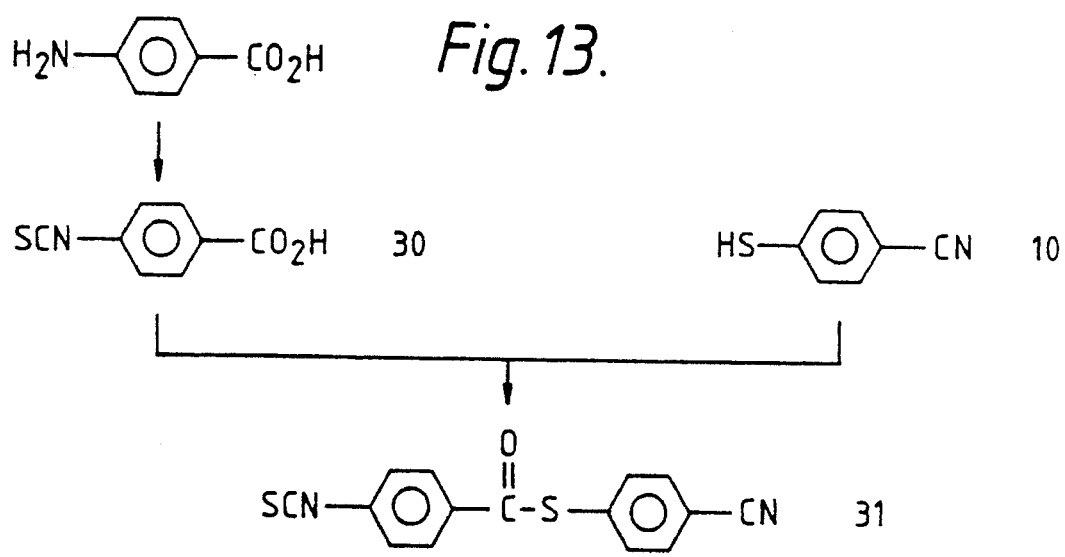
Figure 14:
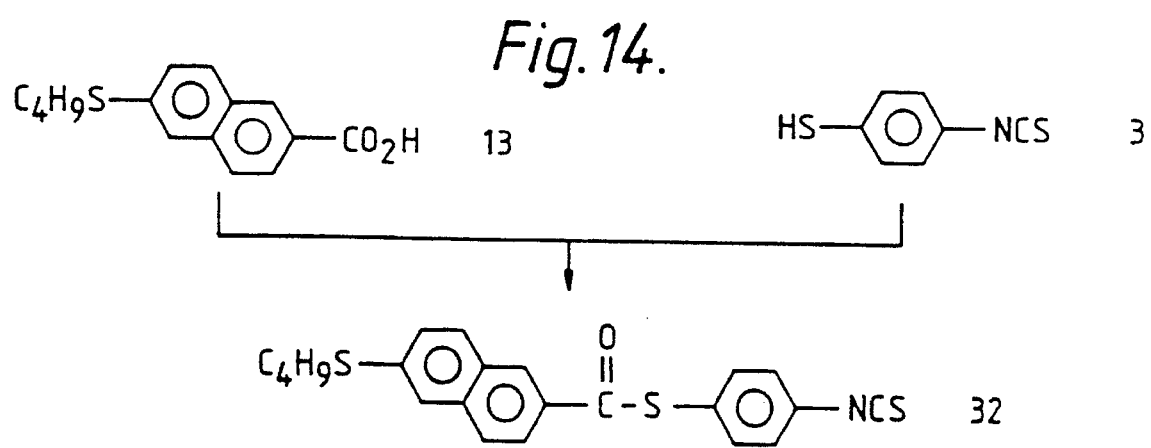

According to this invention, liquid crystal compounds of formula I are provided:

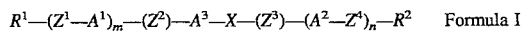

$$R^1-(Z^1-A^1)_m-(Z^2)-A^3-X-(Z^3)-(A^2-Z^4)_n-R^2 \quad \text{Formula I}$$

wherein X is selected from:

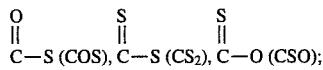

each of $Z^1$, $Z^2$, $Z^3$ and $Z^4$ are independently selected from phenyl, substituted phenyl, where substitution is lateral substitution selected from F, Cl, Br, $NO_2$, CN, NCS; naphthalene substituted naphthalene, where substitution is lateral substitution selected from F, Cl, Br, $NO_2$, CN, NCS, $CH_3$; thiophene, pyridine and pyrimidine;

each of $A^1$ and $A^2$ is independently selected from single bond. $C\equiv C$, $C=CH$;

$A^3$ is selected from $C\equiv C$ and single bond;

each of $R^1$ and $R^2$ are independently selected from CN, NCS, $CH=C(CN)_2$, $C\equiv C-CN$, $C\equiv C-CF_3$, alkyl, alkoxy, thioalkyl, alkenyl, and alkynyl;

m and n are independently selected from 1 and 0, and except where m and n are O, X is COS and each of $R^1$ and $R^2$ are selected from alkyl and alkoxy $A^3$ is a single bond and each of $Z^2$ and $Z^3$ is phenyl provided that when m=n=0, $Z^2=Z^3$=phenyl, X=COS, $A^3$=single bond and one of $R^1$ or $R^2$ is thioalkyl then the other of $R^1$ or $R^2$ does not equal alkyl or alkoxy; and further provided that when X=COS; $Z^2=Z^3$=phenyl; $A^1$ and $A^2$, if present, are both single bonds; $A^3$ is a single bond; $Z^1$ and $Z^4$ if present are phenyl; then $R^1$ and $R^2$ are the same or different and at least one of $R^1$ and $R^2$ is selected from NCS, $CH=C(CN)_2$, $C\equiv C-CN$, $C\equiv C-CF_3$, alkenyl or alkynyl.

The structural and other preferences are expressed below on the basis of inter alia desirable liquid crystalline characteristics, in particular high birefringence for use in liquid crystal materials.

Preferably, where $R^1$ and/or $R^2$ are alkyl, alkoxy, alkynyl and/or thioalkyl, then they have 1-15 carbon atoms, more preferably 1-9 carbon atoms, and even more preferably 2-5 carbon atoms.

Compounds of formula I are advantageous in that they are characterised by a high birefringence ($\Delta n$).

Overall preferred structures for formula I are those listed below:

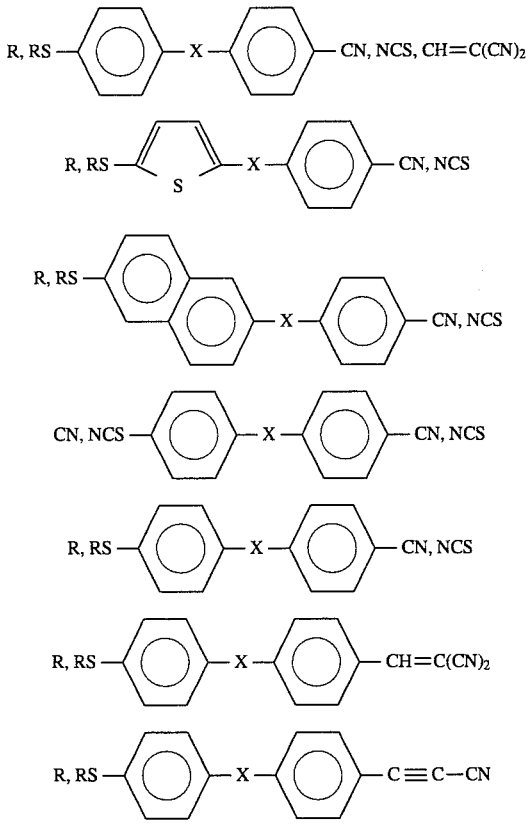

Compounds of formula I can be prepared by various routes. Typically thio-esters where X is COS can be synthesised by esterification of the appropriate benzoic acid and the appropriate thiol compound, via elimination of $H_2O$. Where X is $CS_2$, then such compounds can be prepared using a carbon disulphide reaction with the appropriate Grignard reagent to produce the dithio acid. The acid is then reacted with the appropriate thiol compound. Where X is CSO, then synthesis can be carried out by esterification of the appropriate dithiobenzoic acid with the appropriate hydroxy group. Typical methods of preparation of intermediate compounds will be apparent to those in the art.

A further aspect to this invention is a liquid crystalline material, containing at least two components, at least one of which is a compound of formula I. Compounds of formula I, in particular the preferred compounds referred to above, have a number of desirable properties which make them very useful components of liquid crystal materials, and even more particularly their high birefringence.

Suitable compounds for the other components of the liquid crystal materials will be apparent to those skilled in the field, and will depend upon the properties such as dielectric anisotropy, birefringence, working temperature range etc required in the material for the application for which the material is intended. Some types of suitable material are discussed briefly below.

Preferably as well as containing one or more formula I compounds the mixture contains one or more compounds of formula II.

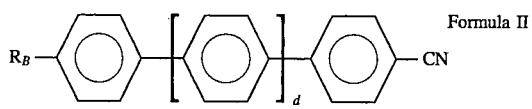

Formula II wherein $R_B$ is alkyl, thioalkyl or alkoxy, preferably containing 1–8 carbon atoms, and preferably straight chain, and wherein d is 1 or 0. Such materials are included in the subject matter of GB 1433130 and GB patent Application Number 90/19268.5. The liquid crystal material may for example contain other liquid crystalline compounds which have a positive dielectric anisotropy, for example as described in EP-A-01322377.

The mixture may also contain such materials as phenyl thiazolines of typical structure such as that seen in Formula III

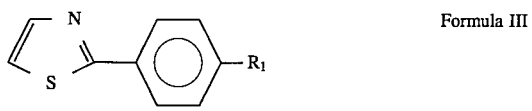

Formula III where typically $R_x$ is CN, alkyl, alkoxy etc.

The material may alternatively or also contain liquid crystalline compounds of low dielectric anisotropy, or a cholesteric mixture which may be thermochromic. Some examples of such compounds are described in EP-A-0132377.

The material may alternatively or also contain liquid crystalline compounds having a high clearing point, for example in order to raise the nematic phase to isotropic phase (N-I) transition temperature. Some examples of such compounds are described in EP-A-0132377.

To cause the material of this aspect of the invention to show a cholesteric or chiral nematic phase the material must contain at least one compound which is optically active. This may be a chiral compound of formula I, or alternatively or also the material may for example contain one or more chiral compounds of formula II above, e.g. S(+) 4-(2-methylbutyl)-4'-cyano biphenyl or S(+) 4-(2-methylbutoxy)-4'-cyano biphenyl.

The material may also contain one or more pleochroic dyes, for example the dyes described in EP-A-82300891.7.

The proportions of these components used in the material of this aspect of the invention will depend upon the intended application, and the material may usefully contain two or more compounds of formula I. If the material does contain two or more compounds of formula I then they may be in proportions that are approximate to a eutectic mixture.

The materials of this aspect of the invention may be used in many of the known forms of liquid crystal display devices, for example a twisted nematic device, Freedericks effect device, cholesteric memory mode device, cholesteric to nematic phase change effect device, dynamic scattering effect device, or a supertwist effect device. The method of construction and operation of such devices, and characteristics of a liquid crystal material suitable for use therein, are well known in the field. Typically an electro-optical display device will consist of 2 substrates between which a layer of the liquid crystal material may be sandwiched. At least one of one substrates is optically transparent and both have addressable electrodes which are preferably made of a transparent material on their opposing faces. By applying an electric field across the layer of liquid crystal material via the electrodes an electro-optical effect is achieved which may be viewed directly or preferably through one or more polarising filters.

Nematic materials of this invention may be particularly suitable for use in ECB effect devices, due to the high birefringence of the materials. They may also be particularly suitable for use in polymer dispersed liquid crystal (PDLC) materials in which small droplets of a liquid crystal material are dispersed within a matrix of a transparent polymer.

This invention provides a further aspect, where compounds of Formula I are suitable for inclusion in devices utilising pretransitional characteristics of liquid crystalline materials in the isotropic phase. Typically such characteristics can be utilised in devices such as Optical Kerr Effect devices. Such devices are often used as optical shutters or optical modulators, and rely on the the fact that birefringence ($\Delta n$) of a medium is proportional to the square of an applied electric field. Such an effect is often termed the quadratic electro-optic effect and can be investigated using degenerate four wave mixing (P Madden et al IEEE J. Quantum Electronics QE22 No 8 Aug 1986 p 1287).

DESCRIPTION OF THE PREFERRED EMBODIMENT

Figure 15:
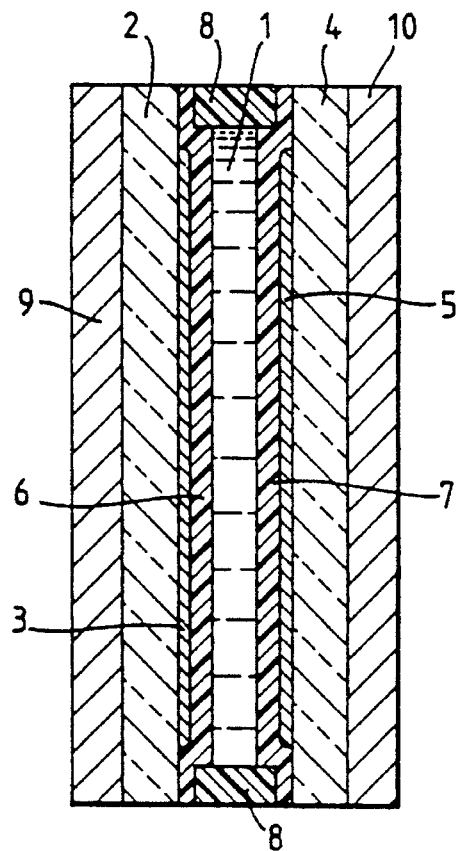
FIG. 15 is a schematic representation of a liquid crystal device of the invention.
Figure 16:
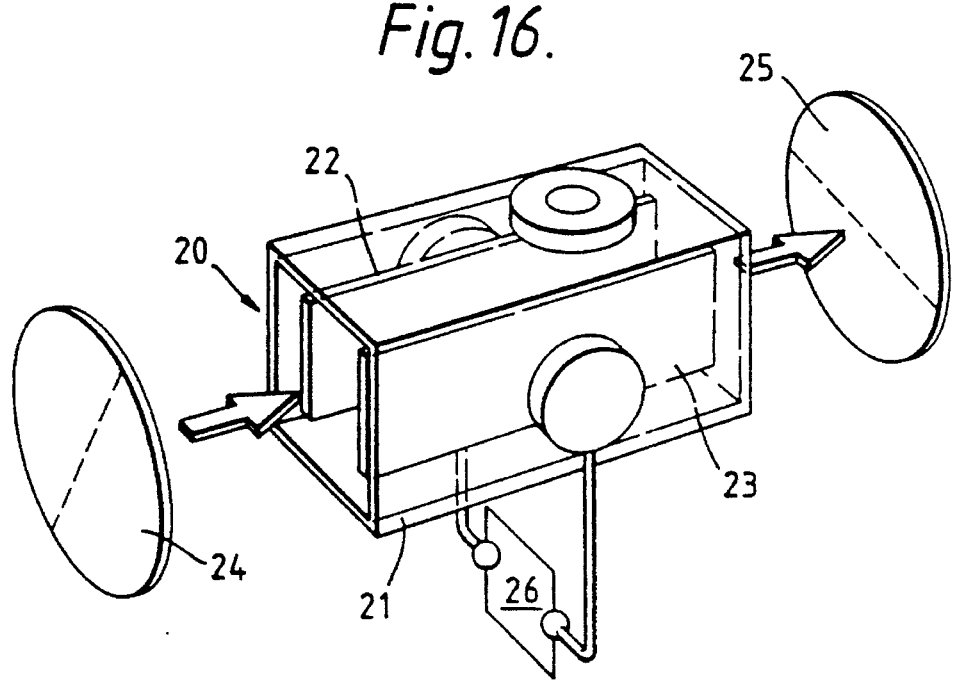
FIG. 16 is a representation of a Kerr cell of the invention.

Non-limiting examples illustrating this invention will now be given, with reference to FIGS. 1–14 giving typical synthesis routes for example compounds of Formula I. FIGS. 15 and 16 are given by way of example only and schematically represent a liquid crystal device of the invention and a Kerr cell of the invention respectively.

EXAMPLE 1

Preparation of S-(4-isothiocyanatophenyl) 4-butylsulphanylthiobenzoate. (4)

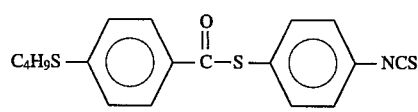

1-Bromo-4-butylsulphanylbenzene (1)

1-Bromobutane (29.04 g, 0.212 mol) was added dropwise to a stirred solution of 4-bromobenzenethiol (20.00 g, 0.106 mol) in sodium ethoxide (2.46 g of sodium metal in 100 ml of super-dry ethanol) at room temperature. The solution was heated at 80° C. for 2 h (glc and tlc analysis revealed a complete reaction) and the sodium bromide was filtered off. The solvent was removed in vacuo and the residue was distilled to give a colourless liquid.

Yield 24.81 g (96%), bp 155°–157° C. at 20 mmHg, purity (glc) >99%.

4-Butylsulphanylbenzoic acid (2)

n-Butyllithium (6.8 ml, 10.0M in hexane, 0.068 mol) was added to a stirred, cooled (−78° C.) solution of compound 1 (16.56 g, 0.067 mol) in dry THF (200 ml), under dry nitrogen at −78° C. The mixture was maintained under these conditions for a further 0.5 h (glc analysis confirmed a complete reaction) before being poured into a slurry of 'Cardice' and dry THF. The mixture was allowed to warm to room temperature overnight. The combined organic extracts were evaporated in vacuo and the residue was dissolved in boiling acetic acid. Ice (400 g) was added to the solution and the product was filtered off and dried in vacuo (KOH, $P_2O_5$).

Yield 10.00 g (71%), mp 113°–114° C.

4-(Isothiocyanato)thiophenol (3)

A solution of 4-aminothiophenol (7.00 g, 0.056 mol) in chloroform (75 ml) was added to a stirred, cooled (0° C.) solution of water (40 ml), chloroform (20 ml), calcium carbonate (6.60 g, 0.066 mol), and thiophosgene (6.95 g, 0.060 mol) at 0°–5° C. The mixture was heated at 35° C. for 1 hour and poured into water (50 ml) before separating the two layers. The organic layer was washed with hydrochloric acid (1%, 100 ml) and dried ($MgSO_4$). The solvent was removed in vacuo to afford an orange semi-solid which was used in the next step without purification.

Yield 8.83 g (95%), purity (glc) >98%.

S-(4-Isothiocyanatophenyl) 4-butylsulphanylthiobenzoate. (4).

N,N'-dicyclohexylcarbodiimide (1.95 g, 0.009 mol), was added in one portion to a stirred solution of compound 2 (1.67 g, 0.008 mol), compound 3 (1.59 g, 0.009 mol) and 4-(N-pyrrolidino)pyridine (0.39 g, 0.003 mol) in dry dichloromethane (50 ml) at room temperature. The reaction mixture was stirred at room temperature overnight. The product was extracted into ether (200 ml) and was washed with aqueous potassium hydroxide solution (5%, 2×250 ml). The ether layer was evaporated in vacuo and the product was purified by column chromatography [silica gel/petroleum fraction (bp 40°–60° C.), dichloromethane, 1:1] and was recrystallised from cyclohexane to afford a white solid which was dried in vacuo.

Yield 1.09 g, (38%), purity (hplc) >99%.

EXAMPLE 2

Preparation of S-(4-Isothiocyanatophenyl) 2-butylsulphanyl-5-thiophenethiocarboxylate. (9)

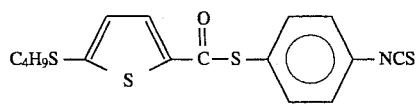

Thiophene-2-thiol (5)

n-Butyllithium (24.0 ml, 10.0M in hexane, 0.24 mol) was added dropwise to a stirred, cooled (−40° C.) solution of thiophene (20.0 g, 0.238 mol) in dry THF (250 ml) at −40° C. under dry nitrogen. The temperature of the reaction mixture was held between −20° and −30° C. for 1 h and then lowered to −78° C. Powdered sulphur (7.62 g, 0.238 mol) was added in one portion and after 30 min the temperature was allowed to rise to −10° C. The solution was poured into rapidly stirred ice water and the organic layer was separated and washed with water (3×100 ml). The combined aqueous extracts were combined with the aqueous layer, cooled, and acidified with sulphuric acid (100 ml, 4.0M). The product was immediately extracted into ether (2×200 ml), and the combined organic extracts were washed with water (500 ml) and dried ($MgSO_4$). The residue was distilled to give a colourless liquid which turned orange on standing. The product was stored under nitrogen.

Yield 15.83 g (57%), bp 60°–64° C. at 20 mmHg.

2-Butylsulphanylthiophene (6)

1-Bromobutane (32.76 g, 0.239 mol) was added dropwise to a stirred solution of compound 5 (13.87 g, 0.120 mol) in sodium ethoxide (2.75 g of sodium metal in 100 ml of super-dry ethanol) at room temperature. The solution was heated at 80° C. for 2 h (glc and tlc analysis revealed a complete reaction) and the sodium bromide was filtered off. The solvent was removed in vacuo and the residue was distilled to give a colourless liquid.

Yield 12.02 g (58%), bp 70°–75° C. at 2 mmHg, purity (glc) >99%.

2-Bromo-5-butylsulphanylthiophene (7)

A solution of compound 6 (5.18 g, 0.030 mol) and N-bromosuccinimide (5.34 g, 0.030 mol) in chloroform (80 ml) and glacial acetic acid (80 ml) was gently heated under reflux (with stirring) for 0.5 h (glc analysis revealed a complete reaction). The reaction mixture was diluted with water and washed with dichloromethane (2×100 ml); the combined organic extracts were washed successively with water (300 ml) and aqueous potassium hydroxide (5%, 300 ml) before being dried ($MgSO_4$). The solvent was removed in vacuo and the residue was distilled to give a colourless liquid.

Yield 6.37 g (88%), bp 104°–108° C. at 2 mmHg, purity (glc) >98%.

2-Butylsulphanyl-5-thiophenecarboxylic acid. (8).

The experimental procedure is as described for compound 2, with use of compound 7 (8.99 g, 0.036 mol) and n-butyllithium (15.0 ml, 2.5M in hexane. 0.037 mol). A white solid was obtained.

Yield 7.78 g, (100%). mp 95°–96° C.

S-(4-Isothiocyanatophenyl) 2-butylsulphanyl-5-thiophenethiocarboxylate. (9)

The experimental procedure is as described for compound 4, and using compound 8 (0.89 g, 0.004 mol), compound 3 (0.61 g, 0.004 mol), N,N'-dicyclohexylcarbodiimide (0.91 g, 0.004 mol), 4-(dimethylamino)pyridine (0.18 g, 0.004 mol). The product was purified by column chromatography [silica gel/petroleum fraction (bp 40°–60° C.). dichloromethane. 1:1] and was recrystallised twice from cyclohexane to afford a white solid which was dried in vacuo.

Yield 0.37 g, (27%), purity (hplc) >99%.

EXAMPLE 3

Preparation of S-(4-Cyanophenyl) 4-butylsulphanylthiobenzoate. (11)

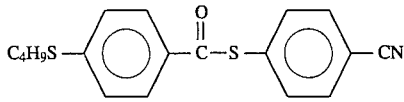

4-Cyanothiophenol (10)

n-Butyllithium (4.4 ml, 10.0M, 0.04 mol) was added dropwise to a stirred, cooled (−100° C.) solution of 4-bromobenzonitrile (7.18 g, 0.039 mol) in dry THF (250 ml) at −100° C. under dry nitrogen. The temperature of the reaction mixture was held at −100° C. for one hour. Powdered sulphur (1.32 g, 0.041 mol) was added in one portion and after 30 minutes the temperature was allowed to rise to -10° C. The mixture was poured into ice and 10% hydrochloric acid. The crude product was extracted into aqueous potassium hydroxide solution (5%, 3×100 ml) and the combined aqueous extracts were washed with ether and acidified with concentrated hydrochloric acid. The product was extracted into ether (2×250 ml) and dried (MgSO₄). The solvent was removed in vacuo to afford a colourless solid.

Yield 2.89 g (55%), mp 41.9°–43.5° C.

S-(4-Cyanophenyl) 4-butylsulphanylthiobenzoate (11).

Quantities: compound 2 (1.04 g, 0.005 mol), compound 10 (0.56 g, 0.004 mol), 4-dimethylaminopyridine (0.20 g, 0.002 mol), N,N'-dicyclohexylcarbodiimide (0.99 g, 0.005 mol).

N,N'-dicyclohexylcarbodiimide (0.99 g, 0.005 mol), was added in one portion to a stirred solution of compound 2 (1.04 g, 0.005 mol), compound 10 (0.56 g, 0.004 mol) and 4-(dimethylamino)pyridine (0.20 g, 0.002 mol), in dry dichloromethane (50 ml) at room temperature. The reaction mixture was stirred at room temperature overnight. The product was extracted into ether (200 ml) and was washed with aqueous potassium hydroxide solution (5%, 2×250 ml). The ether layer was evaporated in vacuo and the product was purified by column chromatography [silica gel/petroleum fraction (bp 40°–60° C.), dichloromethane, 1:1] and was recrystallised from ethanol to afford a white solid which was dried in vacuo (P₂O₅).

Yield 0.72 g (55%), purity (hplc) >99%.

EXAMPLE 4

Preparation of S-(4-Cyanophenyl) 6-butylsulphanyl-2-thionaphthoate. (14)

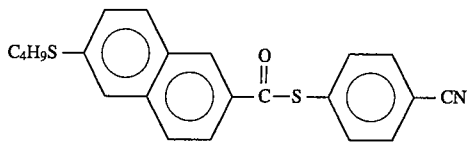

2-Bromo-6-butylsulphanylnaphthalene (12)

Trifluoromethanesulphonic acid (25.00 g, 0.167 mol) was added dropwise to a stirred solution of 6-bromonaphth-2-ol (21.00 g, 0.094 mol) and butane-1-thiol (8.90 g, 0.099 mol) in dry benzene (150 ml), under dry nitrogen. The reaction mixture was stirred for 3 h at 50° C. (glc and tlc analysis revealed a complete reaction), poured into ice cold water (400 ml), and the product was extracted into ether (2×300 ml). The combined organic extracts were washed successively with water (400 ml) and aqueous sodium hydroxide solution (5%, 250 ml) before being dried (MgSO₄). The solvent was removed in vacuo and the product was distilled to afford a white solid.

Yield 16.95 g (61%). bp 160°–162° C. at 0.5 mmHg, mp 39°–41° C. purity (glc) >97%.

6-Butylsulphanylnaphth-2-oic acid (13).

Quantities: compound 12 (5.35 g, 0.018 mol), n-butyl-lithium (7.7 ml. 2.5M in hexane, 0.02 mol).

The experimental procedure was as described for the preparation of compound 2. A white solid was obtained.

Yield 3.05 g (65%), mp 186°–187° C.

S-(4-Cyanophenyl) 6-butylsulphanyl-2-thionaphthoate (14).

Quantities: compound 13 (0.40 g, 0.001 mol), compound 10 (0.17 g, 0.001 mol), 4-dimerhylaminopyridine (0.07 g, 0.006 mol). N,N'-dicyclohexylcarbodiimide (0.31 g, 0.002 mol).

The experimental procedure was as described for compound 11. The product was purified by column chromatography [silica gel/petroleum fraction (bp 40°–60° C.), dichloromethane, 1:1] and was recrystallised from ethanol/ethyl acetate, 20:1 to afford a colourless solid which was dried in vacuo Yield 0.23 g, (51%), purity (hplc) >99%.

EXAMPLE 5

Preparation of S-(4-Isothiocyanatophenyl) 4-pentylthiobenzoate (18).

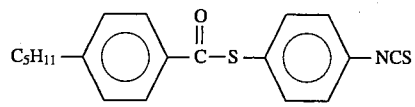

1-Bromo-4-pentanoylbenzene (15).

Valeryl chloride (20.00 g. 0.25 mol) was added dropwise to a stirred, cooled (0° C.) solution of 1-bromobenzene (32.00 g, 0.20 mol) and aluminium chloride (33.00 g, 0.25 mol) at 0° C. The reaction mixture was maintained under these conditions for a further 1 hour and heated at 70° to 80° C. for 2 hours (glc and tlc analysis revealed a complete reaction) before being poured into hydrochloric acid (18%, 200 ml). The product was extracted into dichloromethane (2×200 ml), washed with water and dried (MgSO₄). The solvent was removed in vacuo and the residue was distilled to afford a colourless solid.

Yield 36.00 g (89%), purity (glc) >99%.

1-Bromo-4-pentylbenzene (16).

A mixture of compound 15 (24.87 g, 0.103 mol), hydrazine hydrate (15.45 g, 55% hydrazine content), and diethylene glycol (200 ml), was heated at 130° to 160° C. for 1 hour and water and the excess of hydrazine hydrate were distilled off. The solution was cooled to below 60° C. and potassium hydroxide pellets (17.37 g, 0.309 mol) were added and the solution heated at 200° C. for 2 hours (glc analysis revealed a complete reaction) cooled, and poured into crushed ice (200 g) and hydrochloric acid (200 ml, 6M). The product was extracted into ether (2×200 ml) and dried (MgSO₄). The solvent was removed in vacuo and the residue was distilled to give a colourless liquid.

Yield 19.80 g (85%, purity (glc) >99%.

4-Pentylbenzoic acid (17).

Quantities: compound 16 (5.85 g, 0.026 mol), n-butyl-lithium (11.2 ml, 2.5M in hexane, 0.028 mol).

The experimental procedure was as described for the preparation of e.g. compound 2 (i.e. pour the lithium salt onto cardice and acidify). A white solid was obtained.

Yield 5.04 g (100%), mp 89°–90° C.

S-(4-Isothiocyanatophenyl) 4-pentylthiobenzoate. (18).

Quantities: compound 17 (4.00 g, 0.021 mol), compound 3 (2.59 g, 0.016 mol), N,N'-dicyclohexylcarbodiimide (3.95 g, 0.019 mol), 4-(dimethylamino)pyridine (0.79 g, 0.019 mol).

The experimental procedure was as described for preparation of compound 9. The product was purified by column chromatography [silica gel/petroleum fraction (bp 40°–60° C.). dichloromethane, 1:1] and was recrystallised twice from ethanol to afford a white solid which was dried in vacuo (P₂O₃).

Yield 2.72 g, (50%), purity (hplc) >99%.

EXAMPLE 6

Preparation of 0-(4-cyanophenyl) 4-butylsulphanylthiobenzoate (20).

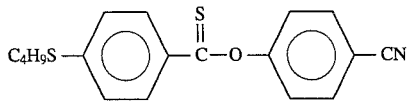

4-Butylsulphanyldithiobenzoic acid. (19)

Compound 1 was slowly added to a stirred mixture of magnesium turnings (2.41 g, 0.100 mol) and dry THF (50 ml) under dry nitrogen at room temperature. 1,2-Dibromomethane (2 drops) was added to initiate the reaction. When the exothermic reaction had subsided the mixture was heated under reflux for 1 hour. The solution was decanted into a dry flask under dry nitrogen and cooled to −10° C. Carbon disulphide (2.76 g, 0.036 mol) was added dropwise at −5° C. and stirring was continued for 3 hours at this temperature. The solution was stirred at room temperature for 1 hour and was poured into ice (100 g) and hydrochloric acid (1M, 100 ml). The crude product was extracted into ether (2×200 ml), washed with sodium hydroxide (5%, 2×200 ml) and the combined aqueous layers were acidified with hydrochloric acid (1M). The product was extracted into ether (2×100 ml). This interconversion of the sodium salt and the free acid was repeated for a further two times before the product was extracted into ether (2×200 ml), washed with water and dried (MgSO$_4$). The solvent was removed in vacuo to afford a purple solid.

Yield 5.91 g (74%), mp 32°–34° C.

0-(4-cyanophenyl) 4-butylsulphanyl thiobenzoate. (20)

Quantities: compound 19 (1.50 g, 0.006 mol), 4-hydroxybenzonitrile (0.59 g, 0.0050 mol), N,N'-dicyclohexylcarbodiimide (1.24 g, 0.006 mol), 4-dimethylaminopyridine (0.25 g, 0.002 mol).

The experimental procedure was as described for the preparation of compound 4. The product was purified by column chromatography [silica gel/petroleum fraction (bp 40° C.–60° C.), dichloromethane, 1:1] and was recrystallised from ethanol to afford golden crystals which were dried in vacuo (P$_2$O$_5$).

Yield 0.67 g (41%), purity (hplc) >99%.

EXAMPLE 7

Preparation of 4-cyanophenyl 4-butylsulphanyldithiobenzoate. (21)

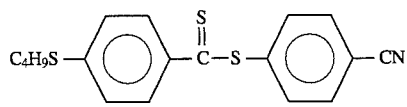

Quantities: compound 19 (1.50 g, 0.006 mol), compound 10 (0.67 g, 0.005 mol), N,N'-dicyclohexylcarbodiimide (1.24 g, 0.006 mol), 4-(dimethylamino)pyridine (0.25 g, 0.002 mol).

The experimental procedure was as described for the preparation of compound 4. The product was purified by column chromatography [silica gel/petroleum fraction (bp 40° C.–60° C.), dichloromethane, 1:1] and was recrystallised from ethanol/ethyl acetate, 3:1 to afford red crystals which were dried in vacuo (P$_2$O$_5$).

Yield 0.58 g (34%), purity (hplc) >99%.

EXAMPLE 8

Preparation of 0-4-Isothiocyanatophenyl 4-butylsulphanylthiobenzoate. (23)

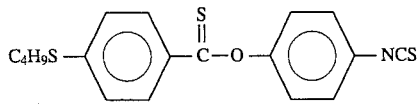

4-Hydroxyphenylisothiocyanate. (22)

4-Aminophenol (21.83 g, 0.200 mol) in pyridine (100 ml) was added dropwise to a stirred, cooled (−10° C.) solution of carbon disulphide (102.14 g, 1.34 mol), N,N'-dicyclohexylcarbodiimide (41.26 g, 0.200 mol) and pyridine (20 ml) at −10° C. under dry nitrogen. The mixture was maintained under these conditions for a further 3 hours and was then stirred at room temperature for 3 hours (glc analysis revealed a 90% reaction). The solution was filtered and the filtrate was washed with hydrochloric acid (200 ml, 1M), water (200 ml) and dried MgSO$_4$). The solvent was removed in vacuo and the crude product was recrystallised from benzene/petroleum ether (bp 40°–60° C.), 1:1 to afford an off-white solid.

Yield 15.77 g, (52%), mp 40°–41° C., purity (glc) >99%.

0-4-Isothiocyanatophenyl 4-butylsulphanylthiobenzoate. (23)

N,N'-Dicyclohexylcarbodiimide (0.41 g, 2.0 mmol) was added in one portion to a stirred solution of compound 19 (1.14 g, 5 mmol), compound 22 (0.25 g, 1.6 mmol) and 4-(dimethylamino)pyridine (0.08 g, 6.56 mmol) in dry dichloromethane (50 ml) at room temperature. The reaction mixture was stirred at room temperature overnight and the N,N'-dicyclohexylurea was filtered off. The filtrate was washed successively with potassium hydroxide (2×200 ml, 5%), water (200 ml), acetic acid (200 ml, 5%), water (200 ml) and dried (MgSO$_4$). The solvent was removed in vacuo and the product was purified by column chromatography [silica gel/petroleum fraction (bp 40°–60° C.), dichloromethane, 1:1] and was recrystallised from petroleum fraction to afford golden crystals which were dried in vacuo (P$_2$O$_5$).

Yield 0.46 g, (75%), purity (hplc) >99%.

EXAMPLE 9

Preparation of 4-Isothiocyanatophenyl 4-butylsulphanyldithiobenzoate (24)

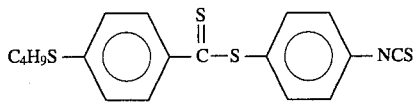

Compound 24 was prepared in a similar way to that described for the preparation of compound 23.

Quantities: compound 19 (1.17 g, 5 mmol) compound 3 (0.65 g, 3.9 mmol), N,N'-dicyclohexylcarbodiimide (0.96 g, 4.7 mmol), 4-(dimethylamino)pyridine (0.19 g, 1.5 mmol).

The product was purified by column chromatography [silica gel/petroleum fraction (bp 40°–60° C.), dichloromethane, 5:1] and was recrystallised from petroleum fraction (bp 40°–60° C.)/ethyl acetate 20:1 to afford red crystals which were dried in vacuo (P$_2$O$_5$)

Yield 0.40 g (27%), purity (hplc) >99%.

EXAMPLE 10

Preparation of S-4-cyanophenyl 4-pentylthiobenzoate. (25)

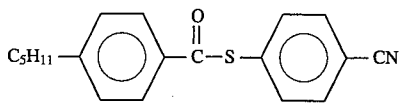

Compound 25 was prepared in a similar way to that described for the preparation of compound 23.

Quantities: compound 17 (0.51 g, 3.8 mmol), compound 10 (0.87 g, 4.5 mmol), 4-(dimethylamino)pyridine (0.19 g, 1.6 mmol). N,N'-dicyclohexylcarbodiimide (0.94 g, 4.6 mmol).

The product was purified by column chromatography [silica gel/petroleum fraction (bp 40°–60° C.), dichloromethane, 1:1] and was recrystallised from ethanol to afford colourless crystals which were dried in vacuo ($P_2O_5$).

Yield 0.70 g (60%), purity (hplc) >99%.

EXAMPLE 11

Preparation of 4-Cyanophenyl 6-butylsulphanyldithionapth-2-oate. (27)

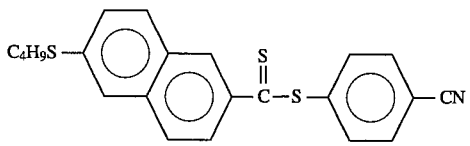

6-Butylsulphanyldithionapth-2-oic acid. (26)

Compound 26 was prepared in a similar manner to compound 19 except that the formation of the Grignard required heating under reflux for 2 hours.

Compound 12 (3.71 g, 0.013 mol), magnesium turnings (0.94 g, 0.039 mol), carbon disulphide (1.09 g, 0.014 mol). A purple solid was obtained.

Yield: 0.73 g (19%), mp 46°–47° C.

4-Cyanophenyl 6-butylsulphanyldithionapth-2-oate. (27)

Quantities: compound 26 (0.28 g, 0.96 mmol), compound 10 (0.10 g, 0.74 mmol), N,N'-dicyclohexylcarbodiimide (0.24 g, 1.2 mmol), 4-(dimethylamino)pyridine (0.05 g, 0.40 mmol).

The product was purified by column chromatography [silica gel/petroleum fraction (bp 40°–60° C.), dichloromethane, 1:1] and was recrystallised from petroleum fraction (bp 40°–60° C.)/ethyl acetate, 1:1 to afford red crystals which were dried in vacuo ($P_2O_5$).

Yield 0.05 g (17%), purity (hplc) >99%.

EXAMPLE 12

Preparation of S-4-Isothiocyanatophenyl 4-cyanothiobenzoate. (29)

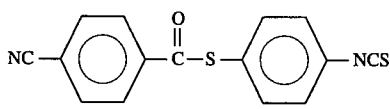

4-Cyanobenzoic acid. (28)

Compound 28 was prepared in a similar manner to that described for compound 17 except that the n-butyllithium was added at −90° C. to −100° C.

S-4-Isothiocyanatophenyl 4-cyanothiobenzoate. (29)

Compound 29 was prepared in a similar manner to that described for the preparation of compound 34.

Quantities: compound 3 (1.98 g, 0.012 mol), compound 28 (0.63 g, 4.3 mmol), 4-(dimethylamino) pyridine (0.29 g, 2.3 mmol), N,N'-dicyclohexylcarbodiimide (1.46 g, 7 mmol).

The product was purified by column chromatography [silica gel/petroleum fraction (bp 40°–60° C.). dichloromethane, 1:1] and was recrystallised from ethanol/ethyl acetate, 1:2 to afford a white solid which was dried in vacuo ($P_2O_5$).

Yield 0.45 g (35%). purity (hplc) >99%.

EXAMPLE 13

Preparation of S-4-Cyanophenyl 4-isothiocyanatothiobenzoate. (31)

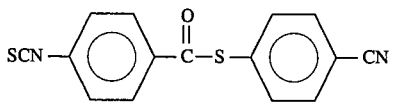

4-Isothiocyanatobenzoic acid. (30)

Compound 30 was prepared in a similar manner to that of compound 3 except that THF was used as a solvent and water and calcium carbonate were omitted from the reaction mixture.

Quantities: 4-Aminobenzoic acid (8.00 g, 0.058 mol), thiophosgene (7.72 g, 0.067 mol).

The product was recrystallised from ethanol/water, 50:1 to afford an off-white solid which was dried in vacuo ($P_2O_5$).

Yield: 4.65 g, (45%), mp>300° C.

S-4-Cyanophenyl 4-isothiocyanatothiobenzoate. (31)

Compound 31 was prepared in a similar manner to that of compound 23.

Quantities: Compound 10 (1.06 g, 8 mmol), compound 30 (0.78 g, 4.4 mmol), N,N'-dicyclohexylcarbodiimide (1.08 g, 5 mmol), 4-(dimethylamino)pyridine (0.22 g, 1.8 mmol). The product was purified by column chromatography [silica gel/petroleum fraction (bp 40°–60° C.), dichloromethane, 5:1] and was recrystallised from ethyl acetate/dimethoxyethane, 10:1 to afford white crystals which were dried in vacuo ($P_2O_5$)

Yield 0.17 g, (13%), purity (hplc) >99%.

EXAMPLE 14

Preparation of S-4-Isothiocyanatophenyl 6-butylsulphanylthionaphth-2-oate. (32)

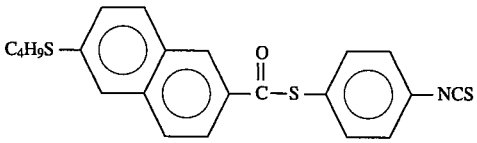

Quantities: compound 3 (0.64 g, 2.0 mmol), compound 13 (0.33 g, 1.9 mmol), 4-(dimethylamino)pyridine (0.10 g, 0.80 mmol), N,N'-dicyclohexylcarbodiimide (0.50 g, 2.4 mmol).

The product was purified by column chromatography [silica gel/petroleum fraction (bp 40°–60° C.). dichloromethane, 5:1] and was recrystallised from ethyl acetate to afford white crystals which were dried in vacuo ($P_2O_5$).

Yield 0.60 g, (77%), purity (hplc) >99%.

Liquid crystal transition temperatures between crystalline (K), nematic (N), smectic A ($S_A$) and isotropic (I) are given in Table 1 for compounds of Formula I. The table also contains birefringence ($\Delta n$), order parameter (S) and a comparison of anisotropy in polarisability ($\Delta \alpha$) with that of 4'-cyano-4-pentylbiphenyl. [ ] denotes a virtual phase transition. $A_1$ is known as a figure of merit and may be evaluated using four wave mixing experiments.

TABLE 1

| COMPOUND. | | PHASE TRANSITION TEMPS (° C.) | Δn | S | Δα | A₁ |
|---|---|---|---|---|---|---|
| C₄H₉S—⟨⟩—C(=O)—S—⟨⟩—NCS | | K 75.9 (S_A 56.4) N 81.3 I | 0.350 | 0.65 | 4.42 | 3.69 |
| C₄H₉S—[thiophene]—C(=O)—S—⟨⟩—NCS | | K 89.3 [N 12] I | 0.290 | 0.44 | 5.50 | 5.62 |
| C₄H₉S—⟨⟩—C(=O)—S—⟨⟩—CN | | K 92.6 N 94.6 I | 0.296 | 0.71 | 3.12 | 2.02 |
| C₄H₉S—[naphthalene]—C(=O)—S—⟨⟩—CN | | K 115.0 N 160.7 I | 0.343 | 0.64 | 4.59 | 3.79 |
| C₅H₁₁—⟨⟩—C(=O)—S—⟨⟩—NCS | | K 58.9 (S_A 38.1) N 76.2 I | 0.294 | 0.66 | 3.46 | 2.37 |
| C₄H₉S—⟨⟩—C(=O)—O—⟨⟩—CN | | K 92.9 [N 5] I | 0.263 | 0.57 | 3.42 | 2.42 |
| C₄H₉S—⟨⟩—C(=O)—S—⟨⟩—CN | | K 111.1 (N 70.9) I | 0.396 | 0.67 | 4.65 | 4.27 |
| NC—⟨⟩—C(=O)—S—⟨⟩—NCS | | K 156.1 N 176.5 I | 0.334 | 0.65 | 3.50 | 2.80 |
| C₄H₉S—[naphthalene]—C(=O)—S—⟨⟩—NCS | | K 90.7 S_A 94.3 N 136.1 I | 0.391 | 0.68 | 5.37 | 4.78 |
| C₄H₉S—[naphthalene]—C(=S)—S—⟨⟩—CN | | K 154.0 N 169.4 I | 0.591 | 0.59 | 8.97 | 13.89 |
| C₄H₉S—⟨⟩—C(=S)—S—⟨⟩—NCS | | K 72.0 (N 34.4) I | 0.396 | 0.65 | 5.23 | 4.95 |
| C₅H₁₁—⟨⟩—C(=O)—S—⟨⟩—CN | | K 76.4 N 101.5 I | 0.231 | 0.73 | 2.22 | 1.09 |
| SCN—⟨⟩—C(=O)—S—⟨⟩—CN | | K 194.3 (N 175.2) I | | | | |

TABLE 1-continued

| COMPOUND. | PHASE TRANSITION TEMPS (° C.) | Δn | S | Δα | $A_1$ |
|---|---|---|---|---|---|
| 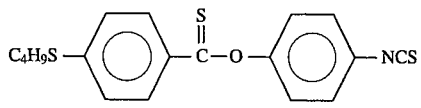 | K 70.5 [N −20] I | 0.265 | 0.50 | 4.33 | 3.54 |

The Δn measurements are normalized for 25° C. and were carried out using an Abbe refractometer and using 3 wt. % of the compound to be measured in a non-polar eutectic nematic host, typically such as

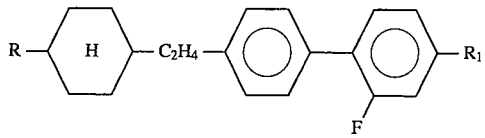

where R and $R_1$ are alkyl.

FIG. 15, a liquid crystal cell, comprises a layer 1 of liquid crystal material, where the material is a mixture incorporating compounds of formula I, sandwiched between a glass slide 2 having a conducting layer 3 on its surface, e.g. of indium tin oxide, and a glass slide 4 having a transparent conducting layer 5 on its surface. The slides 2, 4 bearing the layers 3, 5 are respectively coated with films 6, 7 of a polyimide layer. Prior to construction of the cell the films 6 and 7 are rubbed with a soft tissue in a given direction, the rubbing directions being arranged parallel to the construction of the cell. A spacer 8 e.g. of polymethylmethacrylate, separates the slides 2, 4 to the required distance e.g. 5 microns. The liquid crystal material 1 is introduced between the slides 2, 4 by filling the space between the slides 2, 4 and spacer 8 and sealing the spacer 8 in a vacuum in a known way.

A polarizer 9 is arranged with its polarization axis parallel to the rubbing direction on the films 6, 7 and an analyzer (crossed polariser) 10 is arranged with its polarization axis perpendicular to that rubbing direction. When a voltage is applied across the cell by making contact with the layers 3 and 5 the cell is switched.

In an alternative device (not shown) based on a cell construction as shown in FIG. 15 the layers 3 and 5 may be selectively etched in a known way, e.g. by photoetching or deposition through a mask, e.g. to provide one or more display symbols. e.g. letters, numerals, words or graphics and the like as conventionally seen on displays. The electrode portions thereby may be addressed in a variety of ways which include multiplexed operation.

FIG. 16 shows a Kerr cell 20. It comprises a glass cell 21 having two electrodes 22 and 23, which can be filled with a polar isotropic medium such as compounds of formula I or materials comprising mixtures including at least one compound of formula I. The cell 20 can be positioned between crossed linear polarisers 24 and 25, whose transmission axes are arranged to be at ±45° to an applied electric field. Where there is zero voltage across the electrodes 22 and 23, then the cell 20 acts as a closed shutter. The application of a modulating electric field from voltage source 26 generates an electric field causing the cell 20 to act as a variable wave plate and thus operating as a variable aperture shutter where opening is proportional to the electric field.

We claim:
1. A liquid crystal compound of the formula

$$R^1(Z^1)_m(Z^2)X(Z^3)(Z^4)_nR^2$$

wherein each of $R^1$ and $R^2$ is independently selected from the group consisting of CN, NCS, SCN, $C_{1-16}$ alkyl, $C_{1-16}$ alkoxy and $C_{1-16}$ thioalkyl;

X is selected from the group consisting of COS, CSS and CSO;

$Z^1$ and $Z^4$ are independently selected from the group consisting of phenyl and substituted phenyl, where substitution is lateral substitution selected from F and Cl;

m and n are independently 0 or 1;

$Z^2$ and $Z^3$ are independently selected from the group consisting of naphthalene, substituted naphthalene wherein substitution is lateral substitution selected from F and Cl; phenyl, substituted phenyl wherein substitution is lateral substitution selected from F and Cl and thiophene;

provided that when m=n=0, $Z^2$=$Z^3$=phenyl, X=COS and one of $R^1$ or $R^2$ is thioalkyl then the other of $R^1$ or $R^2$ does not equal alkyl or alkoxy;

provided that when X=COS, $Z^2$=$Z^3$=phenyl, $Z^1$ and $Z^4$ if present are phenyl, then $R^1$ and $R^2$ are the same or different and at least one of $R^1$ and $R^2$ is selected from NCS; provided that when X=COS, m=0, n=0, $R^1$ and $R^2$ are chosen from alkyl, alkoxy or CN then $Z^2$ and $Z^3$ are not chosen from a combination of phenyl and substituted phenyl, phenyl and phenyl, substituted phenyl and substituted phenyl; and provided that if X is CSS then at least one of $R^1$ and $R^2$ is $C_{1-16}$ thioalkyl.

2. A liquid crystal compound according to claim 1 wherein m+n=0.

3. A liquid crystal compound according to claim 1 where $Z^3$ is phenyl.

4. A liquid crystal compound according to claim 1 where $Z^2$ is selected from:

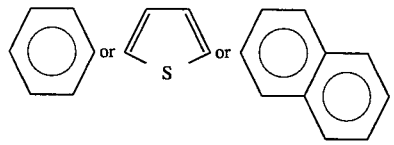

5. A liquid crystal compound according to claim 1 where each of $R^1$ and $R^2$ is selected from the group consisting of alkyl, thioalkyl, CN and NCS.

6. A liquid crystal compound according to claim 5 where one of $R^1$ and $R^2$ is selected from the group consisting of thioalkyl and alkyl.

7. A liquid crystal material, being a mixture of at least two compounds, where at least one compound is a compound of claim 1.

8. A liquid crystal device comprising two spaced cell walls enclosing a layer of liquid crystal material with electrodes on the cell walls wherein the liquid crystal material is a compound of the formula

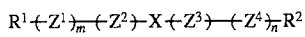

wherein each of $R^1$ and $R^2$ is independently selected from the group consisting of CN, NCS, SCN, $C_{1-16}$ alkyl, $C_{1-16}$ alkoxy and $C_{1-16}$ thioalkyl;

X is selected from the group consisting of COS, CSS and CSO;

$Z^1$ and $Z^4$ are independently selected from the group consisting of phenyl and substituted phenyl, where substitution is lateral substitution selected from F and Cl;

m and n are independently 0 or 1;

$Z^2$ and $Z^3$ are independently selected from the group consisting of naphthalene, substituted naphthalene wherein substitution is lateral substitution selected from F and Cl; phenyl, substituted phenyl wherein substitution is lateral substitution selected from F and Cl and thiophene;

provided that when m=n=0, $Z^2$=$Z^3$=phenyl, X=COS and one of $R_1$ or $R^2$ is thioalkyl then the other of $R^1$ or $R^2$ does not equal alkyl or alkoxy;

provided that when X=COS, $Z^2$=$Z^3$=phenyl, $Z^1$ and $Z^4$ if present are phenyl, then $R_1$ and $R_2$ are the same or different and at least one of $R^1$ and $R^2$ is selected from NCS;

provided than when X=COS, m=0, n=0, $R^1$ and $R^2$ are chosen from alkyl, alkoxy or CN then $Z^2$ and $Z^3$ are not chosen from a combination of phenyl and substituted phenyl, phenyl and phenyl, substituted phenyl and substituted phenyl; and provided that if X is CSS then at least one of $R_1$ and $R^2$ is $C_{1-16}$ thioalkyl.

9. A liquid crystal device utilizing pretransitional characteristics of liquid crystalline compounds wherein said liquid crystalline materials comprise at least one compound of the formula

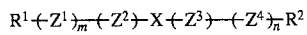

wherein each of $R^1$ and $R^2$ is independently selected from the group consisting of CN, NCS, SCN, $C_{1-16}$ alkyl, $C_{1-16}$ alkoxy and $C_{1-16}$ thioalkyl;

X is selected from the group consisting of COS, CSS and CSO;

$Z^1$ and $Z^4$ are independently selected from the group consisting of phenyl and substituted phenyl, where substitution is lateral substitution selected from F and Cl;

m and n are independently 0 or 1;

$Z^2$ and $Z^3$ are independently selected from the group consisting of naphthalene, substituted naphthalene wherein substitution is lateral substitution selected from F and Cl; phenyl, substituted phenyl wherein substitution is lateral substitution selected from F and Cl and thiophene;

provided that when m=n=0, $Z^2$=$Z^3$=phenyl, X=COS and one of $R^1$ or $R^2$ is thioalkyl then the other of $R^1$ or $R^2$ does not equal alkyl or alkoxy;

provided that when X=COS, $Z^2$=$Z^3$=phenyl, $Z^1$ and $Z_4$ if present are phenyl, then $R_1$ and $R_2$ are the same or different and at least one of $R^1$ and $R^2$ is selected from NCS; provided than when X=COS, m=0, n=0, $R^1$ and $R^2$ are chosen from alkyl, alkoxy or CN then $Z^2$ and $Z^3$ are not chosen from a combination of phenyl and substituted phenyl, phenyl and phenyl, substituted phenyl and substituted phenyl; and provided that if X is CSS then at least one of $R^1$ and $R^2$ is $C_{1-16}$ thioalkyl.

* * * * *